US010383559B2

(12) United States Patent
Leskowich et al.

(10) Patent No.: US 10,383,559 B2
(45) Date of Patent: Aug. 20, 2019

(54) BLOCKING MECHANISM FOR A PATIENT'S SKIN INCISION DEVICE AND A METHOD OF CONTROLLING OF A SKIN INCISION DEVICE BY A BLOCKING MECHANISM

(71) Applicant: HTL-STREFA SPOLKA AKCYJNA, Ozorkow (PL)

(72) Inventors: Vincent Leskowich, Karpathos (GR); Marcin Rozwadowski, Warsaw (PL); Brian E. Jenkins, Cummings, GA (US); David Zou, Zhejiang (CN)

(73) Assignee: HTL-STREFA SPOLKA AKCYJNA, Ozorkow (PL)

( * ) Notice: Subject to any disclaimer, the term of this patent is extended or adjusted under 35 U.S.C. 154(b) by 463 days.

(21) Appl. No.: 15/109,412

(22) PCT Filed: Feb. 17, 2014

(86) PCT No.: PCT/IB2014/059042
§ 371 (c)(1),
(2) Date: Jun. 30, 2016

(87) PCT Pub. No.: WO2015/121711
PCT Pub. Date: Aug. 20, 2015

(65) Prior Publication Data
US 2016/0331292 A1 Nov. 17, 2016

(30) Foreign Application Priority Data
Feb. 14, 2014 (PL) .......................... 407180

(51) Int. Cl.
*A61B 5/15* (2006.01)
*A61B 5/151* (2006.01)

(52) U.S. Cl.
CPC ...... *A61B 5/150374* (2013.01); *A61B 5/1411* (2013.01); *A61B 5/1433* (2013.01);
(Continued)

(58) Field of Classification Search
CPC .......... A61B 5/150374; A61B 5/15107; A61B 5/1411; A61B 5/15142; A61B 5/15113; A61B 5/150442; A61B 5/15117
See application file for complete search history.

(56) References Cited

U.S. PATENT DOCUMENTS

| 4,539,988 A | 9/1985 | Shirley et al. |
| 4,643,189 A | 2/1987 | Mintz |

(Continued)

FOREIGN PATENT DOCUMENTS

WO 2010014044 A1 2/2010

OTHER PUBLICATIONS

Search Report by the Polish Patent Office dated Oct. 8, 2014, issued in priority application No. PL-407180.
(Continued)

*Primary Examiner* — Katrina M Stransky
*Assistant Examiner* — Michael G Mendoza
(74) *Attorney, Agent, or Firm* — Wentsler LLC

(57) ABSTRACT

The invention relates to a blocking mechanism for a skin incision device and to a method of controlling of a skin incision device by a blocking mechanism. The blocking mechanism comprises a blocking means and a trigger means, which by, respectively, a fixing means and a locating means are mounted in a housing of the cooperating incision device, and which are provided with an engaging means configured to cooperate mutually with each other so that an inadvertent firing of the blocking mechanism and an inadvertent actuation of the incision device prior to use of the device as well as a re-use of the device is not possible, and an indication of a state of use of the device by the blocking means and the trigger means is unambiguous.

18 Claims, 4 Drawing Sheets

(52) U.S. Cl.
CPC .... *A61B 5/150022* (2013.01); *A61B 5/15107* (2013.01); *A61B 5/15113* (2013.01); *A61B 5/15117* (2013.01); *A61B 5/15128* (2013.01); *A61B 5/15142* (2013.01); *A61B 5/150442* (2013.01); *A61B 5/150503* (2013.01); *A61B 5/150916* (2013.01)

(56) References Cited

U.S. PATENT DOCUMENTS

| | | |
|---|---|---|
| 5,314,441 A | 5/1994 | Cusack et al. |
| 5,797,940 A | 8/1998 | Mawhirt et al. |
| 5,951,582 A | 9/1999 | Thorne et al. |
| 6,042,595 A | 3/2000 | Morita |
| 2006/0106411 A1 | 5/2006 | Schraga |
| 2007/0293882 A1 | 12/2007 | Harttig et al. |
| 2010/0168776 A1 | 7/2010 | Schraga |
| 2011/0144682 A1 | 6/2011 | Hong |
| 2011/0264131 A1* | 10/2011 | Sun ................. A61B 5/1411 606/182 |

OTHER PUBLICATIONS

International Search Report and Written Opinion of the International Searching Authority dated Oct. 17, 2014 in Application No. PCT/IB2014/059042.

Written Opinion of the International Preliminary Examining Authority dated Feb. 11, 2016 in Application No. PCT/IB2014/059042.

International Preliminary Report on Patentability dated May 25, 2016 in Application No. PCT/IB2014/059042.

* cited by examiner

BLOCKING MECHANISM FOR A PATIENT'S SKIN INCISION DEVICE AND A METHOD OF CONTROLLING OF A SKIN INCISION DEVICE BY A BLOCKING MECHANISM

BACKGROUND OF THE INVENTION

Field of the Invention

The present invention relates to a blocking mechanism for a patient's skin incision device, particularly for a disposable skin incision device, and to a method of controlling of a skin incision device by a blocking mechanism.

State of Art

There are known patient's skin incision devices, disposable ones, for collecting a blood sample for diagnostic purposes, which perform an incision of a skin with a determined geometry of the incision that is with the determined length, depth and the profile of the incision, and which are prevented from an unintentional actuation and/or from a re-use.

From the patent publication No. U.S. Pat. No. 5,314,441 there is known an incision device with a lever assembly provided with a planar blade, which blade performs a rotary-plane motion, controlled by respectively formed guides in the housing. The device is prevented from an inadvertent actuation by a blocking mechanism configured in an upper portion of a housing. The blocking mechanism comprises a trigger slidably disposed in the housing, which cooperates with the lever assembly, and a removable safety clip situated between the trigger and the housing. For the actuation of the incision device, there is a necessity to remove the safety clip and, afterwards, to press the trigger deep into the inside of the housing. After detachment of the safety clip from the trigger and its removal from the incision device, the trigger moves freely into the inside of the housing and back outside, after actuation of the device and after its use as well. With such a structure of the blocking mechanism, after use of the device, the trigger can be freely pulled out back in the front direction that is outside the device and the safety clip can again be located between the trigger and the housing, as a result of which a state of use of the device is not unambiguous for the user. Such a structure of the blocking mechanism with a removable component part, here in the form of the safety clip, which for the actuation of the device has to be taken out of the device, imposes upon the user focusing on this component part and acting consciously in order to put it aside and to utilize it safely, the acting which has to be safe first of all because of the patient but also because of an environment. Moreover, such a structure imposes upon the user employment of both hands to operate the device, which makes impossible to hold reliably and continuously a segment of the patient's body, which is to be incised, or to hold the whole patient and the selected segment of his or her body as in the case of a premature baby, newborn, baby or a small child, which can cause a risk for the patient.

From the patent publication No. U.S. Pat. No. 6,042,595 there is known an incision device for executing a precisely controlled incision on a patient's body, in which a blade before a use of the device is protected by a removable shield and a motion of the blade is controlled by slide guides in a housing. The device comprises a two-stage mechanism of an actuation of an incision stroke of the blade with the first stage, in which an arm of a trigger is in a ready-to-fire state, and with the second stage, in which the arm of the trigger is in a firing state. Before the use of the device and for the firing of the actuation mechanism, the shield has to be removed from the blade and then remains detached from the device without any possibility to put it again on the blade, which imposes upon the user operating the device with a closed attention and causes utilization problems. The described incision device requires two hands to operate it, and is not provided with a blocking mechanism precluding, on purpose, from an inadvertent actuation of the device.

SUMMARY OF THE INVENTION

The Objects of the Invention

It is desirable to design a reliable blocking mechanism for preventing an inadvertent actuation of the patient's skin incision device before its intended use and once it is used.

It is an object of the present invention to work out a blocking mechanism for a patient's skin incision device, which on the one hand will simplify an operation of the device and on the other hand will guarantee a safety for the patient by developing a structure which enables to operate and to actuate the incision device comfortably with a single hand only. With a structure obtaining the aforementioned object, the user, for example, a medical professional, will have a better control of the patient during performing the skin incision, namely, one user's hand will be able to hold safely a heel of the patient, for example, a newborn, in a desired position and the second hand will be able to operate the device. Such a structure of the blocking mechanism will increase a comfort of the operating with the skin incision device.

The next object of the present invention is to provide such a blocking mechanism for the incision device, which will not comprise any removable component parts necessary to be taken out for a firing the blocking mechanism and for an actuation of the skin incision device, which enables to obtain the safe incision device which after its use will be utilized in its entirety.

It is the further object of the present invention to provide the blocking mechanism which will unambiguously indicate a state of use of the incision device. This object can be carried out by the blocking mechanism in which positions of movable component parts after use of the incision device will be determined that is stationary.

Another object of the present invention is to provide the blocking mechanism to be applied in the disposable incision device, and thus such that its structure elements cooperating with structure elements of the lever assembly for actuation of the incision device will be configured so that a re-use of the device will be excluded.

Another object of the present invention is to provide the blocking mechanism with a simple and cheap structure comprising possibly small amount of component parts to reduce manufacture costs of a final product that is the skin incision device and to make its utilization after use easier, which has a primary significance in case of medical devices intended for mass medical applications.

The other objects of the present invention will become clear in the light of the following detailed description and accompanying drawings.

The Essence of the Invention

The blocking mechanism, according to the present invention, for a skin incision device, particularly for a disposable incision device, comprises a blocking means for controlling of a firing of the blocking mechanism, which is mounted by a fixing means in a housing of the device and is movable from a locking position to a non-locking position, and a trigger means for controlling of an actuation of the incision device, which is mounted by a locating means in the housing of the device, and is movable from an initial position to a final position and is configured to cooperate with a lever assembly driving a blade with a cutting edge of the incision device, which lever assembly is affixed to the housing of the device, wherein for preventing an inadvertent firing of the blocking mechanism and for preventing an inadvertent actuation of the incision device, and for preventing against a re-use of the incision device and for ensuring of an unambiguous indication of a state of use of the device, the blocking means and the trigger means are provided with an engaging means configured to mutually cooperate with each other so that the blocking means and the trigger means, before the actuation of the device, are in their respective positions mutually fixed, and, after the actuation of the device, are in their respective positions mutually fixed and stationary in permanent non-reversible mutual engagement with each other.

Preferably, for the firing of the blocking mechanism and the actuation of the incision device by an exclusively single finger of exclusively the same single hand, with which exclusively a single user operates during a complete operation of the device, the blocking means and the trigger means are configured as non-removably mounted in the housing of the device within a reach of the said single finger and are in turn moved, first the blocking means into its non-locking position and then the trigger means into its final position.

Preferably, with the blocking means in the locking position and with the trigger means in the initial position, the blocking mechanism is in a locked state and the incision device is in a pre-use state with the lever assembly immobilized and the blade completely hidden inside the housing, and with the blocking means in the non-locking position and with the trigger means in the initial position, the blocking mechanism is in a ready-to-fire state and the incision device is in a pre-actuated state with the lever assembly immobilized and the blade completely hidden inside the housing, and with the blocking means in the non-locking position and with the trigger means in the final position, the blocking mechanism is in a firing state and the incision device is, first, in an actuated state with the lever assembly released and the blade executing a skin incision, and, then, in an after-use state with the lever assembly immobilized and the blade completely hidden inside the housing.

Preferably, the blocking means comprises a blocking push-button and is movable from the locking position constituting an upper position to the non-locking position constituting a lower position and a trigger means comprises a trigger and is movable from the initial position constituting a protruded position to the final position constituting a pressed position.

Preferably, for the cooperation with the lever assembly driving the blade with the cutting edge, the trigger means has the lower surface which is provided with an offset shaped into a form of a cavity for receiving an upper portion of the lever assembly.

Preferably, the fixing means comprises a flexible boss and a catch on the blocking means and an abutting shoulder on the housing.

Preferably, the locating means comprises an initial locating projection and a final locating projection on the trigger means and an abutment on the housing.

Preferably, the engaging means comprises a rib on the trigger means and a blocking surface and a recess on the blocking means.

A method of controlling, according to the present invention, of a skin incision device by a blocking mechanism according to the present invention, the method comprises steps of:

(I) providing the blocking mechanism to the skin incision device with a blocking means and with a trigger means, which is being mounted in a housing of the incision device by, respectively, a fixing means and a locating means, for fixing their positions in the housing, and which is being moved from, respectively, a locking position and the initial position, to, respectively, a non-locking position and a final position, for a firing of the blocking mechanism and for an actuation of the incision device by cooperation of the trigger means with a lever assembly driving a blade with a cutting edge of the incision device, which lever assembly is being affixed in the housing of the device, and which is being provided with an engaging means configured to mutually cooperate with each other, respectively, for preventing an inadvertent firing of the blocking mechanism and for preventing an inadvertent actuation of the incision device by mutual fixing of their positions, before the actuation of the device, and for preventing against a re-use of the incision device and for ensuring of an unambiguous indication of a state of use of the device by mutual fixing and making stationary of their positions in permanent and non-reversible mutual engagement with each other, after the actuation of the device;

(II) verifying the state of use of the incision device by checking the positions of the blocking means and the trigger means, which should be situated, respectively, in the locking position and in the initial position;

(III) gripping the incision device, and placing the device above a place chosen for an incision on the patient's skin;

(IV) moving, in turn, the blocking means as the first one into the non-locking position and the trigger means as the second one into the final position, firing the blocking mechanism and actuating the incision device for performing of the skin incision;

(V) moving the incision device away from the skin after using the device and putting the device aside for utilization.

Preferably, in the course of performing step (I) of the providing the blocking mechanism to the skin incision device, the blocking means and the trigger means are being provided, which are being non-removably mounted in the housing of the device within a reach of exclusively a single finger of exclusively the same single hand with which exclusively a single user operates during a complete operation of the device, for the firing of the blocking mechanism and for the actuation of the device by the said single finger.

Preferably, in the course of performing step (II) of the verification of the state of use of the incision device, the incision device is being put aside for utilization, when the blocking means is in the non-locking position and the trigger means is in the final position, and first, the trigger means is being moved into the final position thereby actuating the incision device, and then the device is being put aside for utilization, when the blocking means is in the non-locking position and the trigger means is in the initial position.

Preferably, in the course of performing step (IV) of moving, in turn, the blocking means as the first one into the non-locking position and the trigger means as the second one into the final position, by leaving the blocking means in the locking position and the trigger means in the initial position, the blocking mechanism is being maintained in a locked state and the incision device is being maintained in a pre-use state with the lever assembly immobilized and the blade completely hidden inside the housing, and by moving the blocking means into the non-locking position and by leaving the trigger means in the initial position, the blocking mechanism is being entered into a ready-to-fire state and the incision device is being maintained in a pre-actuated state with the lever assembly immobilized and the blade completely hidden inside the housing, and by maintaining the blocking means in the non-locking position and by moving the trigger means into the final position, the blocking mechanism is being entered into a firing state and the incision device is being entered, first, in an actuated state with the lever assembly released and the blade executing the skin incision, and, then, into an after-use state with the lever assembly immobilized and the blade completely retracted into the inside of the housing.

Preferably, in the course of performing step (I) of providing the blocking mechanism to the skin incision device, as the blocking means and the trigger means, respectively, a blocking push-button and a trigger is being used, wherein for the locking position and the non-locking position for the blocking means, respectively, an upper position and a lower position for the blocking push-button is being chosen, and for the initial position and the final position for the trigger means, respectively, a protruded position and a pressed position is being chosen.

Preferably, in the course of performing step (I) of providing the blocking mechanism to the skin incision device, for the cooperation with the lever assembly driving the blade with the cutting edge, the trigger means is being configured with a lower surface which is being provided with an offset shaped into a form of a cavity for receiving an upper portion lever assembly.

Preferably, in the course of performing step (I) of providing the blocking mechanism to the skin incision device, as the fixing means, a flexible boss and a catch on the blocking means and an abutting shoulder on the housing is being used.

Preferably, in the course of performing step (I) of providing the blocking mechanism to the skin incision device, as the locating means, an initial locating projection and a final locating projection on the trigger means and an abutment on the housing is being used.

Preferably, in the course of performing step (I) of providing the blocking mechanism to the skin incision device, as the engaging means, a rib on the trigger means and a blocking surface and a recess on the blocking means is being used.

THE ADVANTAGES OF THE INVENTION

The blocking mechanism for the patient's skin incision device obtained according to the present invention is reliable and safe.

The possibility of an inadvertent or unintentional firing of the blocking mechanism and a premature actuation of the incision device, before an intended use, is excluded, because prior to use of the incision device movable component parts of the blocking mechanism that is the blocking means and the trigger means remain in the fixed positions without the possibility of their unintentional or inadvertent displacement, namely, the blocking means in the locking position and the trigger means in the initial position.

Similarly, after the use of the incision device, the movable component parts of the blocking mechanism that is the blocking means and the trigger means remain in the fixed positions that is unchangeable, the blocking means in the non-locking position and the trigger means in the final position, and are with each other immovably and irreversibly mutually engaged. Such a structure enables the user to read off the state of use of the incision device immediately and unambiguously, without the possibility of any mistake.

The blocking mechanism is configured so that it cooperates with the component part of the lever assembly driving the blade with the cutting edge, which is situated on the side of the housing of the incision device opposite relative to the blade, that is the blocking mechanism and an opening for the cutting edge are placed on the opposite sides of the housing, which is safe and convenient for the user.

The blocking mechanism according of the present invention provides for the user of the incision device the full control of the state of use of the device and of its actuation, with simultaneous keeping an absolute safety for the patient and for healthcare workers in accordance with the current requirements set for disposable medical devices.

The important advantage of the present safety blocking mechanism is that it enables to operate the blocking mechanism and the incision device very simply by one hand. The movable component parts of the blocking mechanism designed to be operated by the user are easily available for him or her and are operated by the index finger of the single hand. Due to this the medical professional has the better control of the patient during performing the skin incision, one hand for the whole time holds, for example, a heel of a baby in a desired position and the second hand alone operates the blocking mechanism and the incision device. A nurse, when operating the incision device by one hand, can for the whole time hold the baby's heel with the second hand. She does not need to dedicate her attention to take out any clips, staples or to search around after component parts removed, which slipped out of her grasp and so on. Thus, she has the full control of a patient and of action to incise the skin and to take a blood sample, which superbly increases the safety for the patient and the comfort of the device operation for the user.

The advantage of the present blocking mechanism is that it does not comprise of any removable component parts which would be necessary for taking them out for the firing of the blocking mechanism and for the actuation of the skin incision device and, then, after incision of the skin, for an immobilization of the lever assembly driving the blade. After use of the incision device, there are no any separated component parts. Thus, the blocking mechanism is safe for the patient and comfortable for the user and the incision device after the use is utilized in its entirety.

Another advantage of the blocking mechanism according to the present invention is that its structure elements cooperating with structure elements of the lever assembly of the incision device for the actuation of the device are configured so that another use of the device is excluded.

The blocking mechanism according to the present invention can by applied in many of the skin incision devices of different types, provided that mutual adaptation of the structures of the incision device and the blocking mechanism within the present invention is made.

BRIEF DESCRIPTION OF DRAWINGS

The subject matter of the present invention in a preferred and non-limiting embodiment of a blocking mechanism is presented on the drawings, FIGS. 1-8, wherein.

DETAILED DESCRIPTION OF THE PREFERRED INVENTION EMBODIMENT

A blocking mechanism according to the present invention is built into a housing of a skin incision device and cooperates with a lever assembly driving a blade 9 with a skin cutting edge, as depicted in FIGS. 1-8. The blocking mechanism according to the present invention is designed to be applied in the incision devices of different structures and types, including the disposable incision devices.

In the present description, terms "forward" and "backward" will be used for description of different component parts or elements relating, respectively, the term "forward" to the side where on the housing a pusher of a trigger 3 is situated, which will be operated with the index finger of the single hand, that is to the side of the incision device which is situated, when gripping the device by the user more outside the hand, and the term "backward" to the side of the device situated more inside the hand.

Terms "upper", "lower" will relate, respectively, the term "upper" to the side where on the housing a blocking push-button 4 is situated, which will be operated with the index finger of the single hand, and the term "lower" to the opposite side of the incision device that is the side, on which an opening for the blade 9 with the cutting edge is situated and which is applied to the patient body for the skin incision.

Terms "left", "right" relate to the sides of the device respective and resulting from the above terms "forward" and "backward", "upper" and "lower".

In the following description and the patent claims for the blocking mechanism and the method of controlling of the incision device according to the present invention, the terms used "configured for cooperation", "configured for mutual cooperation with each other" or "configured as" encompasses also meanings "formed or arranged or being configured or adapted respectively for cooperation", "for mutual cooperation with each other" or "formed or arranged or being configured or adapted respectively so that" to perform in a proper way respective indicated functions of individual technical means or component parts or structure elements of the component parts for the correct performance of functions of the whole device.

Figure 1:
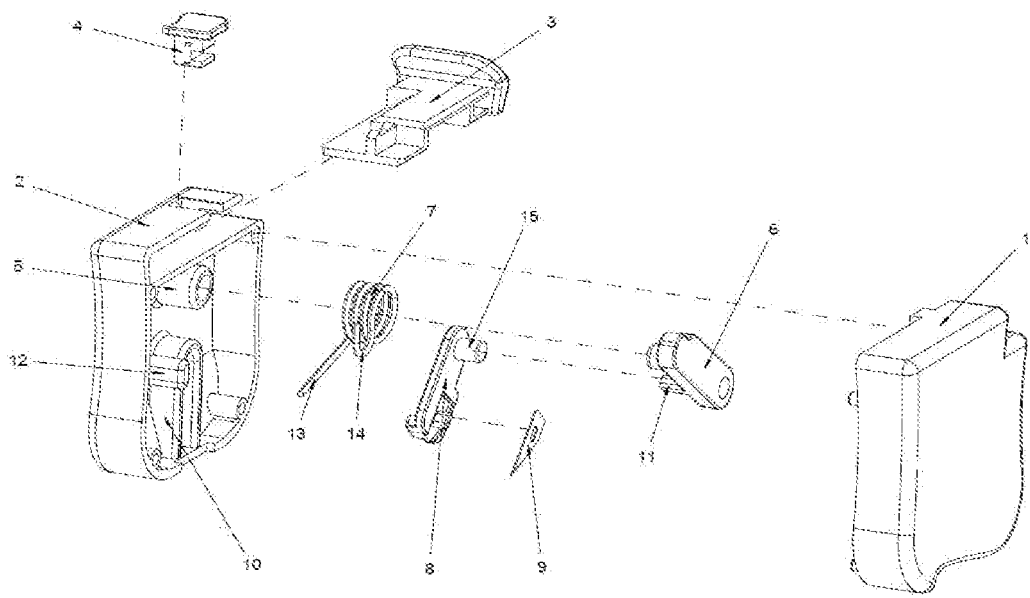
FIG. 1 shows a perspective exploded view of an exemplary skin incision device with a blocking mechanism according to the preferred embodiment of the present invention.

As depicted in FIG. 1, the blocking mechanism, which will be described below in a more detailed manner, comprises in general the blocking push-button 4 and the trigger 3, which are slidably disposed in the upper portion of the housing of the exemplary cooperating incision device. The housing consists of the first half 1 and the second half 2. In upper portions of both halves of the housing, the first half 1 and the second half 2, the trigger 3 is disposed. The lower surface 17 of the trigger 3 is formed respectively for cooperation with a lever arm 6 of the lever assembly, which lever arm 6 cooperates with a support arm 8 for the blade 9 with the cutting edge. The blocking push-button 4 is disposed in a specifically designed cut-off in an upper wall of the second half 2 of the housing. Inside the second half 2, below the trigger 3, on a fixed pivot 5, which is configured on an internal side of a left wall in the second half 2 of the housing, a drive spring 7 is mounted and the lever arm 6 of the lever assembly is rotatably borne. The drive spring 7 is biased in the course of an assembly of the incision device.

A straight end 13 of the drive spring 7 abuts against a stop 12, which is formed on the internal side of the left wall of the housing, and a bend end 14 of the drive spring 7 is caught in a holder 11 on the lever arm 6. By a movable pivot 15 on the support arm 8, the lever arm 6 is rotatably coupled with the support arm 8, to which the blade 9 is affixed. After firing the blocking mechanism and after actuation of the incision device, the lever arm 6 and the support arm 8 with the blade 9 are driven by the released drive spring 7 and are guided by a guide 10 which is formed on the internal side of the left wall of the housing.

Figure 3:
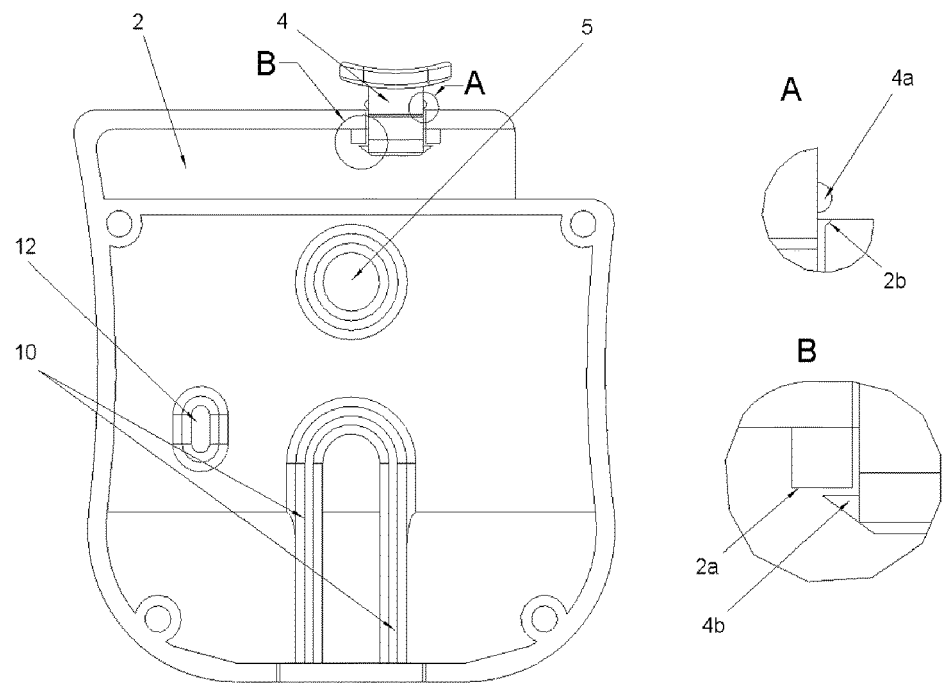
FIG. 3 shows a view of the second half 2 of the housing of the incision device depicted in FIG. 1 in the pre-use state with a blocking push-button 4 of the blocking mechanism depicted in FIG. 1 in an upper position and with an enlarged structure details A, B for showing a fixing means applied for fixing the blocking push-button 4 in a cut-out of an upper wall of the housing.
Figure 4:
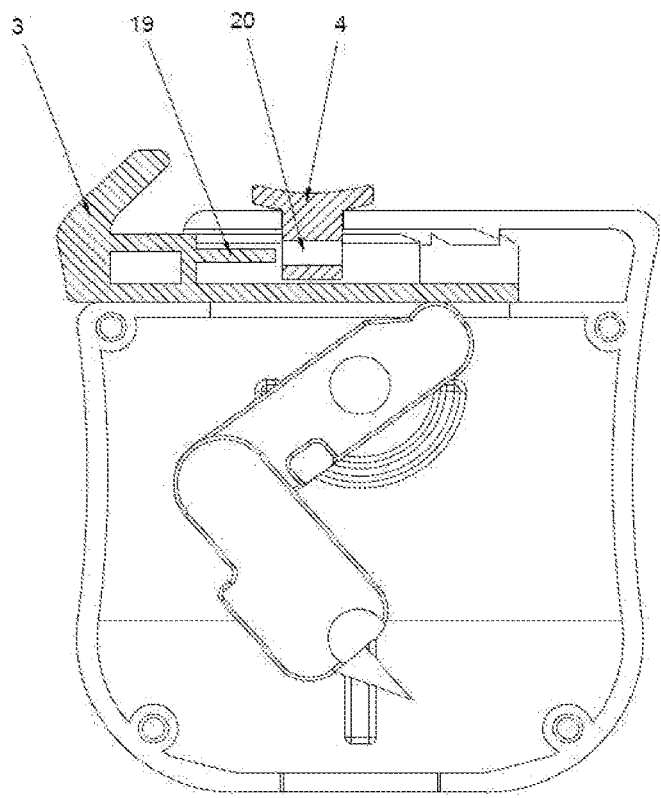
FIG. 4 shows a view of the first half 1 of the housing of the incision device depicted in FIG. 1 in a pre-actuated state and a longitudinal cross-section view of the blocking mechanism depicted in FIG. 1 in a ready-to-fire state, with showing the engaging means for engagement of the blocking push-button 4 with a trigger 3 and a locating means for location of the trigger 3 in a protruded position in the upper wall of the housing.
Figure 8:
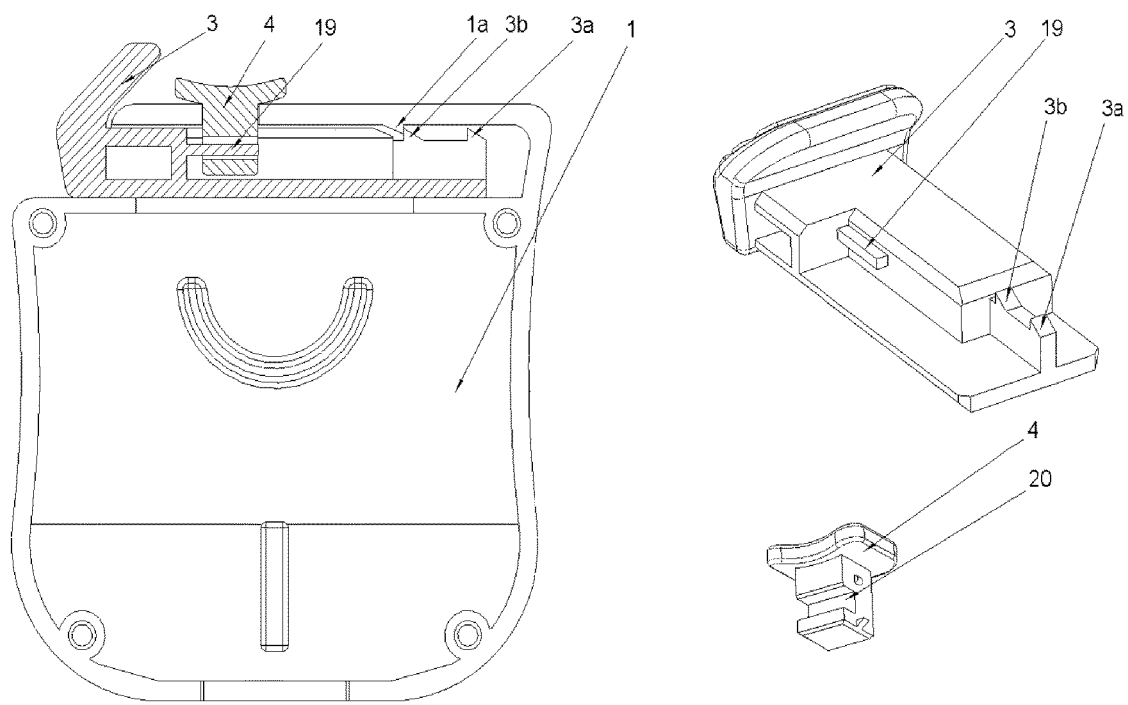
FIG. 8 shows a view of the first half 1 of the housing of the incision device depicted in FIG. 1 and a longitudinal cross-section view of the blocking mechanism depicted in FIG. 1 in the firing state, and perspective views of the blocking push-button 4 and the trigger 3, with showing the engaging means for engagement of the blocking push-button 4 with the trigger 3 and with showing the locating means for location of the trigger 3 in the upper wall of the housing.

The blocking mechanism comprises a blocking means for controlling of a firing of the blocking mechanism, which in this embodiment of the blocking mechanism is in the form of the blocking push-button 4, and which is affixed in the cut-off in the upper wall of the second half 2 by a fixing means, preferably, in the form of a flexible boss 4*a* and a catch 4*b* on the blocking push-button 4 and of an abutting shoulder 2*a* on the lower surface of the upper wall of the second half 2 of the housing, as depicted in FIGS. 3 and 8. Due to the abutting shoulder 2*a*, the blocking push-button 4 can not be taken out, removed or detached from the housing of the device. The blocking means during the assembly of the device is mounted in the housing of the device in its locking position. In order to use the incision device, the blocking means needs to be moved from the locking position to the non-locking position. In this embodiment of the blocking mechanism, the blocking push-button 4 needs to be moved from the upper position home into the lower position, which requires to apply an adequate force to a profiled upper surface of the blocking push-button 4 so that the flexible boss 4*a* is pressed through a guiding undercut 2*b* into the cut-off in the housing, as depicted in FIG. 4. Due to the fixing means, the two operational positions of the blocking means in the housing that is the locking position and the non-locking position, that is the upper position and the lower position of the blocking push-button 4, are fixed, without the possibility of their inadvertent change and without the possibility of disconnection of the blocking push-button 4 from the incision device with which the blocking mechanism cooperates.

Figure 2:
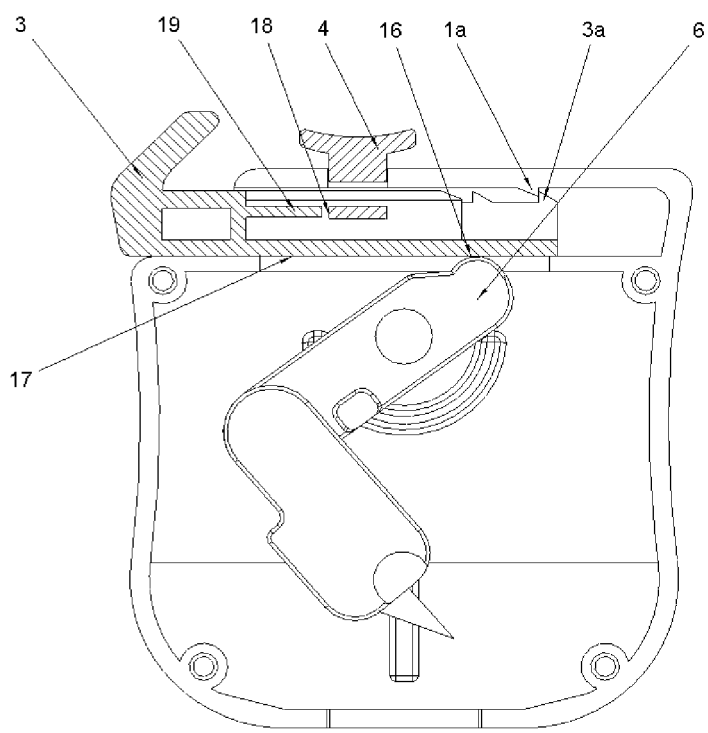
FIG. 2 shows a view of the first half 1 of a housing of the incision device depicted in FIG. 1 in a pre-use state and a longitudinal cross-section view of the blocking mechanism depicted in FIG. 1 in a locked state with showing an engaging means used for engagement of a blocking push-button 4 with a trigger 3.

The blocking mechanism comprises also a trigger means for controlling of an actuation of the incision device, which, in this embodiment of the blocking mechanism, is in the form of the trigger 3 and which is fastened in a channel formed in the upper portion of the housing in the first 1 and the second 2 halves by a locating means, preferably, in the form of an initial locating projection 3*a* and a final locating projection 3*b* on the trigger 3 and in the form of an abutment 1*a* on the lower surface of the upper wall of the first half 1 of the housing, as depicted in FIGS. 2 and 8. The trigger 3 is during the assembly of the device disposed in its protruded position in the first half 1 so that the initial locating projection 3*a* is caught in the abutment 1*a* and taking the trigger 3 out of the housing after the assembly of the device is not possible. In order to use the incision device, the trigger means should be moved from the initial position, in this embodiment from the protruded position that is the forward position, to the final position, in this embodiment to the pressed position that is the backward position. When the trigger 3 is moved into the pressed position, the final locating projection 3*b* is caught in the abutment 1*a* and sliding the trigger 3 out from the housing is not possible, see FIG. 8. By dint of the locating means, the two operational positions of the trigger means in the housing that is the initial position and the final position that is the protruded position and the pressed position of the trigger 3 are fixed, and sliding the trigger 3 out of the housing or detachment of the trigger 3 from the housing of the incision device, with which the blocking mechanism cooperates, is not possible.

The blocking means and the trigger means comprise an engaging means which is configured to mutual cooperation with each other prior to, during and after use of the incision device. In this embodiment of the blocking mechanism, the engaging means is a blocking surface 18 and a recess 20 on the blocking means that is on the blocking push-button 4 and a rib 19 on the trigger means that is on the trigger 3.

In FIG. 2 it is shown, in the longitudinal cross-section, an exemplary incision device with the blocking mechanism according to the preferred embodiment as presented here of the present invention, in a state, in which it is delivered to the user that is in the pre-use state. The blocking push-button 4 is fixed in its upper position and is precluded from falling out of the cut-off in the upper wall of the first half 1 of the housing, as depicted in FIG. 3. The trigger 3 is, by the initial locating projection 3*a* of the trigger 3 abutted against the abutment 1*a* of the housing, fixed in its protruded position and is secured against sliding out from the housing and is, by the rib 19 of the trigger 3 abutted against the blocking surface 18 of the blocking push-button 4, secured against moving deep inside the housing. The blocking mechanism shown in FIG. 2 is in a locked state. Due to such a structure of the blocking mechanism according to the invention, the location of the blocking push-button 4 in the upper position and the trigger 3 in the protruded position, unambiguously indicates to the user that the incision device is in a pre-use state.

The lower surface 17 of the trigger 3 in the locked state of the blocking mechanism contacts a slide surface 16 of the lever arm 6 of the lever assembly and supports the lever arm 6 so that the lever assembly, which is provided with the biased drive spring 7, is immobilized and the blade 9 is safely completely hidden in the housing. The incision device can not be inadvertently actuated. With this type of the incision device cooperating with the blocking mechanism according to the present invention, a removable shield on the cutting edge of the blade 9 is not needed, and thereby the number of the component parts of the complete device is decreased. The cutting edge of the blade 9 is sterilized together with the entire incision device just after its assembly.

In order to use the incision device, first, the blocking push-button 4 has to be displaced into its lower position, and, afterwards, the trigger 3 into its pressed position. The blocking push-button 4 and the trigger 3 are arranged on the housing of the device within a reach of the single finger of the same single hand of the single user and they do not need to be removed or taken out of the housing for use of the incision device, and thereby they do not employ the second hand to actuate the device.

Thus, first, the user by the finger applies to an ergonomically shaped upper surface of the blocking push-button 4 a respective required force and presses the blocking push-button 4 home by moving it to its lower position, as depicted in FIG. 4. At this stage of the device operation, the blocking mechanism is in a ready-to-fire state, the incision device is in a pre-actuated state and the lever assembly is still immobilized with the blade 9 completely hidden inside the housing.

Figure 5:
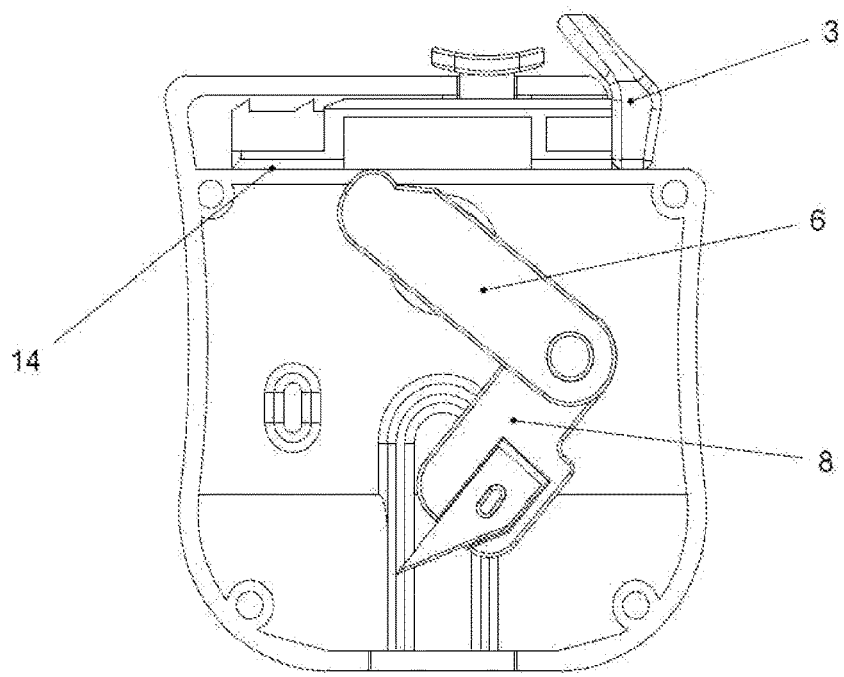
FIG. 5 shows a view of the second half 2 of the housing of the incision device depicted in FIG. 1 in an actuated state and a view of the blocking mechanism depicted in FIG. 1 in a firing state, with a lever assembly released at the beginning of an incision phase.
Figure 6:
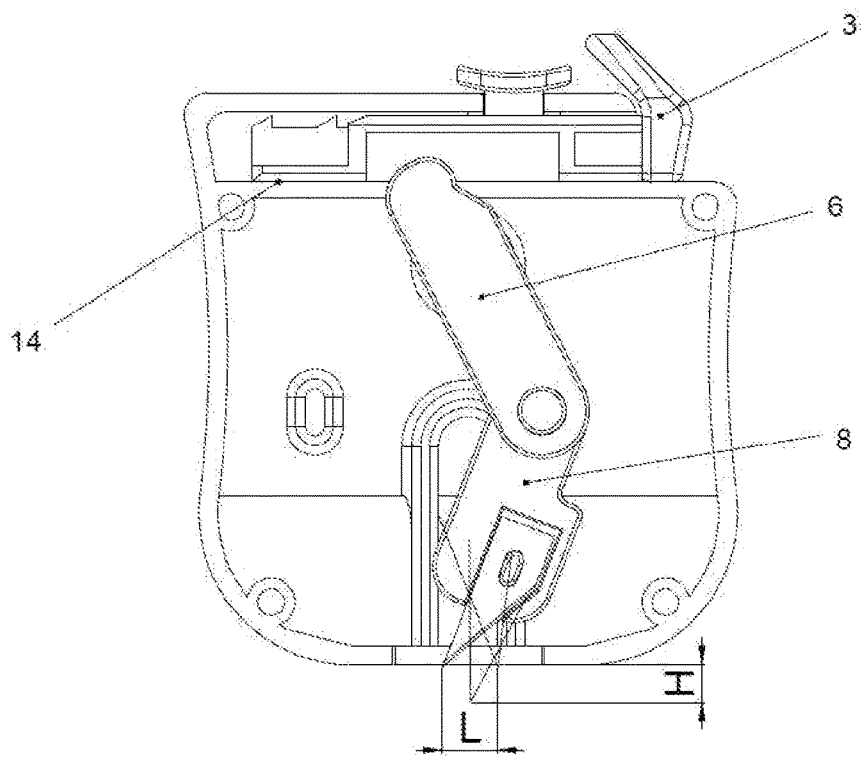
FIG. 6 shows a view of the second half 2 of the housing of the incision device depicted in FIG. 1 in the actuated state and a view of the blocking mechanism depicted in FIG. 1 in the firing state, with the lever assembly released at the moment when a blade 9 commences a skin incision.
Figure 7:
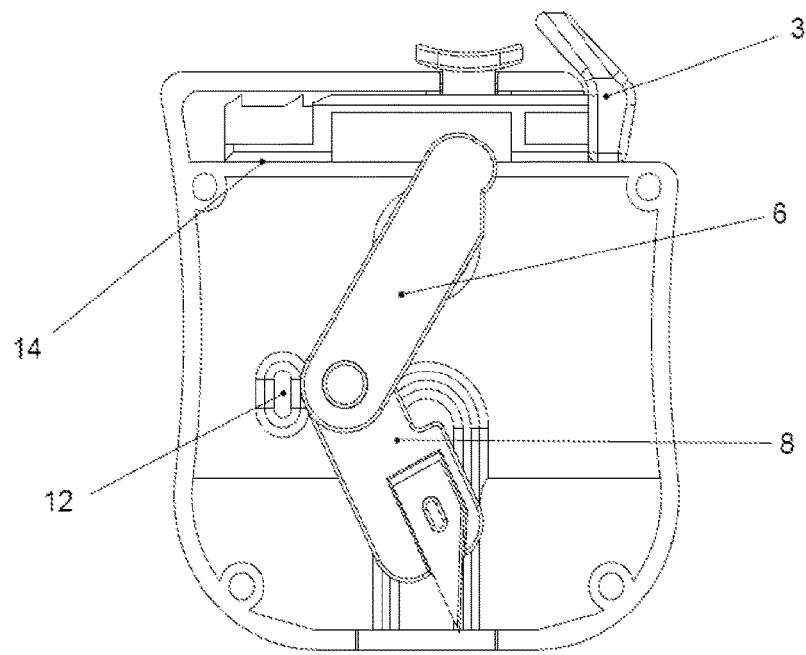
FIG. 7 shows a view of the second half 2 of the housing of the incision device depicted in FIG. 1 in an after-use state and a view of the blocking mechanism depicted in FIG. 1 in the firing state, with the lever assembly immobilized after a completion of the incision phase.

Afterwards, the user, by the same finger of the same hand pushes the trigger 3 in the backward direction into its pressed position that is deep inside the housing. The trigger 3 has a forward part which outer surface is ergonomically shaped, preferably, as an oblique orientated in the forward direction and upwards with formation of a pusher of the trigger 3, conveniently for the user, as depicted in FIG. 4. The trigger 3 is being moved to the pressed position because the rib 19 of the trigger 3 enters freely into a recess 20 of the blocking push-button 4 and the lower surface 17 of the trigger 3 slides freely over the slide surface 16 of the lever arm 6 as far as a place of an offset in the lower surface 17 of the trigger 3, as depicted in FIGS. 5, 6 and 7. The offset, in the upper direction, shaped in the lower surface 17 of the trigger 3 into the form of a cavity, as depicted in FIGS. 5, 6 and 7, is arranged in a portion of the trigger 3 situated after mounting the incision device in the first half 1 of the housing. After the full movement of the trigger 3 into the pressed position, in the moment when the slide surface 16 of the lever arm 6 looses contact with the lower surface 17 of the trigger 3, the lever arm 6 falls into the cavity and the drive spring 7, which was put under the tension in the course of the assembly of the device, starts to drive the lever arm 6. The lever assembly becomes released. The lever arm 6 starts to rotate around a fixed pivot 5 and transmits drive onto a support arm 8 with the blade 9 affixed thereto. The drive from the lever arm 6 is transmitted onto the support arm 8 via, cooperating with each other, a holder 11 and a movable pivot 15, which are situated, respectively, on the lever arm 6 and on the support arm 8. The support arm 8 with the blade 9 during motion are guided in the guide 10 formed onto the internal side of the left wall of the housing in its second half 2. With such a guidance, the cutting edge of the blade 9 performs an incision of a length "L" and a depth "H", which can be designed, respectively to the needs of anticipated customers of the incision device, by adjustment of parameters of the lever assembly including the place of the attachment of the blade 9 to the support arm 8 or the length of the blade 9. In FIGS. 5 and 6, it is shown the blocking mechanism in a firing state and the incision device in an actuated state, wherein FIG. 5 shows the device with the lever assembly released at the beginning of an incision phase and FIG. 6 shows the device in the moment when the blade 9 commences the incision of the skin.

FIG. 7 shows the lever assembly after completion of the incision phase, when the lever assembly is again immobilized upon resting the lever arm 6 on the stop 12 in the left wall of the housing and when the blade 9 is again completely hidden inside the housing. The incision device, as depicted in FIG. 7, is in an after-use state.

As depicted in FIGS. 5-7 and FIG. 8 in the views of the longitudinal cross-section of the blocking mechanism, in the firing state of the blocking mechanism and after the actuation of the incision device, the blocking push-button 4 and the trigger 3 are in its positions, respectively, in the lower position and in the pressed position, which are mutually fixed and unchangeable and are in permanent and non-reversible mutual engagement with each other. Upon the actuation and the use of the skin incision device, the blocking push-button 4, the trigger 3 and the housing, namely, the blocking push-button 4 with the second half 2 of the housing, the trigger 3 with the first half 1 of the housing and the blocking push-button 4 with the trigger 3, are permanently engaged with each other. Due to such a structure of the blocking mechanism according to the invention, the incision device is prevented from re-using it. At the same time, the location of the blocking push-button 4 in the lower position and the trigger 3 in the pressed position, unambiguously indicates to the user that the incision device is in the after-use state. Upon the firing of the blocking mechanism, the actuation of the incision device and the incision of the skin, the blocking push-button 4 is immobilized by the rib 19 of the trigger 3 in the lower position of the blocking push-button 4 and the trigger 3 is immobilized by the final locating projection 3*b* caught in the abutment 1*a* on the upper wall of the first half 1 of the housing in the pressed position of the trigger 3. The lever assembly with the blade 9 is not able to return to the position, from which it could be re-actuated because the drive spring 7 via the lever arm 6 constantly presses the support arm 8 of the blade 9 to the stop 12 in such a manner that after use of the incision device the blade 9 is fully retracted into the inside of the housing. Without disassembly of the incision device, there is no possibility to arm it again. A re-use of the incision device once used is not possible.

The cutting edge prior to and after use of the incision device remains completely hidden inside the housing and thereby any protection shield it is not required.

None of the component parts of, both the blocking mechanism as itself, and of the incision device, is not and does not have to be disconnected from the incision device for firing of the blocking mechanism and for actuation of the incision device.

The blocking mechanism according to the present invention, which comprises the above described component parts and structure elements and which performs functions indicated in the present description, serves for realization of a method of controlling of the skin incision device which is provided with the blocking mechanism. The controlling of the incision device by the blocking mechanism according to the present invention is realized by the user of the incision device and is executed in the course of the operation of the device in accordance with instructions received together with a product.

The controlling of the incision device by the blocking mechanism starts with a verification of the state of use of the incision device by a control of the positions of the blocking push-button 4 and the trigger 3 relative to the housing of the device. The blocking push-button 4 should be situated in its upper position and the trigger 3 should be situated in its protruded position, as depicted in FIG. 2. Such positions of the blocking mechanism 4 and the trigger 3 inform the user that the device was not earlier used and can be safely used. When the blocking push-button 4 and the trigger 3 are situated in different positions than mentioned above, the device should right away be put aside for utilization.

In the case when the incision device is apt for using, the user grabs the incision device with the single hand by the housing in such a way that when the user operates with her or his right hand, the user supports the left wall of the housing in the second half 2 with the thumb and the right wall of the housing in the first half 1 with the middle finger and the index finger remains free to operate the blocking push-button 4 and the trigger 3 for the firing of the blocking mechanism and for the actuation of the incision device. The device grabbed in such a manner should be placed over the place on the patient's skin chosen for the incision and should be moved closer to the skin.

Then, for the firing of the blocking mechanism and the actuation of the incision device, the blocking push-button 4 as the first one should be pressed home deep inside the housing that is moved into its lower position and the trigger 3 as the second one should be pressed home deep inside the housing that is moved to its pressed position. The blocking push-button 4 and the trigger 3 should be moved from their positions shown in FIG. 2 into the positions shown in FIG. 8. Upon the actuation of the incision device, the phase of the skin incision follows, upon which, when finished, the blade 9 is again completely hidden inside the housing, which is safe for the user. At that time, the device should be moved away from the patient's body and should be put aside for utilization.

The user can safely hold the incision device inside the hand and rearrange or change its position in the hand in order to grip the device conveniently prior to and after its use, without fear that she or he inadvertently pricks herself or himself with the blade 9 or inadvertently fires the blocking mechanism off and actuates the device, because the blade 9 before the actuation of the device and after its use is completely and stably hidden inside the housing. The blocking push-button 4 and the trigger 3 cannot be in any way taken out of the housing prior to, during and after use of the device and the upper and the lower positions of the blocking push-button 4 and the protruded and the pressed positions of the trigger 3 are stably fixed in the housing prior to and after use of the device. At the same time, the change of the positions of the blocking push-button 4 and the trigger 3 can be made by the user only under deliberate realization of the above described method of controlling of the incision device with the respective actions performed in the proper sequence and upon applying the respective forces to the blocking push-button 4 and to the trigger 3. With such features of the blocking mechanism according of the present invention, the inadvertent firing of the blocking mechanism and the inadvertent actuation of the incision device prior to its intended use as well as the re-use of the device once used is not possible. Moreover, the state of use of the incision device provided with the blocking mechanism according to the present invention is easy for reading by the user due to observation of the positions of the blocking push-button 4 and the trigger 3. After use of the incision device, the positions of the blocking push-button 4 and the trigger 3 are fixed and stationary whereby it is easy to distinguish the incision device used from the one not used. This is very important for the safety of the patient and medical professional. The mentioned advantages of the blocking mechanism according to the present invention are achieved due to the above described structure of the mechanism and, particularly, due to the fixing means 4a, 4b, 2a, 2b, the locating means 3a, 3b, 1a, the engaging means 19, 18, 20 and the respective configuration of the trigger means 3, in the presented embodiment of the blocking mechanism in the form of the trigger 3, for the cooperation with the lever assembly driving the blade 9 with the cutting edge of the incision device prior to, during and after use of the device.

Additionally, neither the blocking mechanism according to the present invention nor the incision device comprise any removable component parts that is the parts which can inadvertently fall out or slip out or the parts which need to be taken out or disconnected from the blocking mechanism or from the incision device in order to use the device. At the same time, the blocking push-button 4 and the trigger 3 are situated on the adjacent walls of the housing in its upper portion that is close to each other, wherein outer surfaces of the blocking push-button 4 and the trigger 3 are respectively ergonomically shaped for reliable contact with the finger to fire the blocking mechanism and to actuate the incision device easily. Due to this, the complete operation of the incision device with the blocking mechanism is realized exclusively by the single hand of the single user and displacements of the blocking push-button 4 and the trigger 3 deep inside the housing for actuation of the device are realized by the single finger of the same hand, preferably, by the index finger. Moreover, the forward and backward outer surfaces and the outer surfaces of the right and left walls in the both halves, the first one 1 and the second one 2, of the housing are also respectively ergonomically shaped for reliable contact with the fingers that is with the thumb, the middle and the ring finger of the hand. In the effect, the user by the single hand firmly holds and safely operates the incision device.

Thereby, controlling of the incision device by the blocking mechanism according to the invention is safe, simple, convenient and comfortable for the patient, medical professional and the environment.

LIST OF COMPONENT PARTS AND STRUCTURE ELEMENTS

1. First half of the housing
1a. Abutment
2. Second half of the housing
2a. Abutting shoulder
2b. Guiding undercut
3. Trigger
3a. Initial locating projection
3b. Final locating projection
4. Blocking push-button
4a. Flexible boss
4b. Catch
5. Fixed pivot
6. Lever arm
7. Drive spring
8. Blade support arm
9. Blade
10. Guide
11. Holder
12. Stop
13. Straight end of the drive spring 7
14. Bend end of the drive spring 7
15. Movable pivot
16. Slide surface of the lever arm 6
17. Lower surface of the trigger 3
18. Blocking surface of the blocking push-button 4
19. Rib of the trigger 3
20. Recess in the blocking push-button 4

The invention claimed is:

1. A skin incision device comprising:
a housing;
a push-button mounted to the housing in an initial push-button position, wherein the push-button is configured to be moved relative to the housing to be mounted to the housing in a final push-button position;
a trigger mounted to the housing in an initial trigger position, wherein the initial push-button position of the push-button provides an initial contact between the trigger and the push-button to prevent the trigger from moving relative to the housing to a final trigger position; and
a spring-loaded linkage biased against the trigger in the initial trigger position while supporting a cutting edge of a blade within the housing,
wherein the trigger is configured to be moved to the final trigger position relative to the housing after the push-button is moved to the final push-button position relative to the housing to fire the spring-loaded linkage to extend the cutting edge of the blade outside of the housing and then retract the cutting edge of the blade back within the housing.

2. The skin incision device of claim 1, wherein the trigger is configured to be locked relative to the housing in the final trigger position by an engagement between the trigger and the housing.

3. The skin incision device of claim 2, wherein the trigger is configured to be locked relative to the housing in the final trigger position by an abutment.

4. The skin incision device of claim 1, wherein the trigger is configured to block movement of the push-button from the final push-button position to the initial push-button position.

5. The skin incision device of claim 4, wherein a rib of the trigger is configured to be received within a recess of the push-button to block movement of the push-button from the final push-button position to the initial push-button position.

6. The skin incision device of claim 1, wherein a recess of the push-button is configured to be aligned with a rib of the trigger when the push-button is mounted to the housing in the final push-button position.

7. The skin incision device of claim 1, wherein the push-button is configured to translate in a linear direction of a push-button path to move the push-button from the initial push-button position to the final push-button position.

8. The skin incision device of claim 7, wherein the trigger is configured to translate in a linear direction of a trigger path to move the trigger from the initial trigger position to the final trigger position, wherein the linear direction of the push-button path is perpendicular to the linear direction of the trigger path.

9. The skin incision device of claim 1, wherein the trigger is configured to translate in a linear direction of a trigger path to move the trigger from the initial trigger position to the final trigger position.

10. The skin incision device of claim 1, wherein an upper portion of spring-loaded linkage is configured to be received within a cavity of the trigger to cause firing of the spring-loaded linkage when the trigger is moved to the final trigger position.

11. A method of firing the skin incision device of claim 1 comprising:
    moving the push-button from the initial push-button position to the final push-button position; and then
    moving the trigger from the initial trigger position to the final trigger position, while the push-button remains in the final push-button position, to fire the spring-loaded linkage wherein the cutting edge of the blade extends outside of the housing and then the cutting edge of the blade is retracted back within the housing.

12. The method of claim 11, wherein a user moves the push-button from the initial push-button position to the final push-button position with a finger of the user, and wherein the user moves the trigger from the initial trigger position to the final trigger position with the same finger.

13. The method of claim 11, wherein after moving the trigger from the initial trigger position to the final trigger position, the trigger is locked with the housing from moving from the final trigger position to the initial trigger position.

14. The method of claim 13, wherein after moving the trigger from the initial trigger position to the final trigger position, the trigger prevents the push-button from moving from the final push-button position to the initial push-button position.

15. The method of claim 11, wherein after moving the trigger from the initial trigger position to the final trigger position, the trigger prevents the push-button from moving from the final push-button position to the initial push-button position.

16. The method of claim 11, wherein the push-button is translated in a linear direction of a push-button path when moving the push-button from the initial push-button position to the final push-button position.

17. The method of claim 16, wherein the trigger is translated in a linear direction of a trigger path when moving the trigger from the initial trigger position to the final trigger position, wherein the linear direction of the push-button path is perpendicular to the linear direction of the trigger path.

18. The method of claim 11, wherein the trigger is translated in a linear direction of a trigger path when moving trigger from the initial trigger position to the final trigger position.

* * * * *

UNITED STATES PATENT AND TRADEMARK OFFICE
CERTIFICATE OF CORRECTION

Page 1 of 1

PATENT NO. : 10,383,559 B2
APPLICATION NO. : 15/109412
DATED : August 20, 2019
INVENTOR(S) : Vincent Leskowich et al.

It is certified that error appears in the above-identified patent and that said Letters Patent is hereby corrected as shown below:

On the Title Page

Item (73) Assignee:
"HTL-STREFA SPOLKA AKCYJNA, Ozorkow (PL)"
Should read:
--HTL-STREFA SPOLKA AKCYJNA, Ozorkow (PL); GLOBAL RESOURCES INTERNATIONAL, INC., Flowery Branch, GA (US)--

Signed and Sealed this
Tenth Day of March, 2020

Andrei Iancu
*Director of the United States Patent and Trademark Office*